United States Patent
Oda et al.

(10) Patent No.: US 12,029,835 B2
(45) Date of Patent: Jul. 9, 2024

(54) NEEDLELESS ACCESS CONNECTOR WITH ANTIMICROBIAL RESISTANT VALVE

(71) Applicant: CareFusion 303, Inc., San Diego, CA (US)

(72) Inventors: Todd Oda, San Diego, CA (US); George Mansour, San Diego, CA (US); Ali Saleh, San Diego, CA (US); Tomas Frausto, San Diego, CA (US); Siddarth K. Shevgoor, San Diego, CA (US); Archana Nagaraja Rao, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 817 days.

(21) Appl. No.: 16/785,342

(22) Filed: Feb. 7, 2020

(65) Prior Publication Data

US 2021/0244859 A1    Aug. 12, 2021

(51) Int. Cl.
*A61L 29/16*    (2006.01)
*A61K 31/155*    (2006.01)
(Continued)

(52) U.S. Cl.
CPC ............ *A61L 29/16* (2013.01); *A61K 31/155* (2013.01); *A61L 29/085* (2013.01); *A61M 39/02* (2013.01); *A61M 39/10* (2013.01); *A61M 39/24* (2013.01); *A61M 39/26* (2013.01); *A61L 2300/206* (2013.01); *A61L 2300/404* (2013.01); *A61M 2039/0036* (2013.01);
(Continued)

(58) Field of Classification Search
CPC .. A61L 29/16; A61L 29/085; A61L 2300/206; A61L 2300/404; A61K 31/155; A61M 39/02; A61M 39/10; A61M 39/24; A61M 39/26; A61M 2039/0036; A61M 2039/027; A61M 2039/0285; A61M 2205/0205
See application file for complete search history.

(56) References Cited

U.S. PATENT DOCUMENTS 5,707,366 A    1/1998    Solomon et al.
6,171,287 B1    1/2001    Lynn et al.
(Continued)

FOREIGN PATENT DOCUMENTS

CA    2745158    6/2010
WO    WO-2008014447 A2    1/2008
(Continued)

OTHER PUBLICATIONS

International Search Report and Written Opinion for Application No. PCT/US2021/016668, dated May 19, 2021, 12 pages.
(Continued)

*Primary Examiner* — Lauren P Farrar
(74) *Attorney, Agent, or Firm* — Morgan, Lewis & Bockius LLP

(57) ABSTRACT

A valve including an antimicrobial agent can be used with needleless access connectors. The valve can have an insert that includes an antimicrobial coating thereon and/or the valve can have physical features, such as a series of tunnels or groves or a patterned surface, containing an antimicrobial formulation and/or the valve can be made of a material that includes an antimicrobial agent.

19 Claims, 5 Drawing Sheets

(51) Int. Cl.
*A61L 29/08* (2006.01)
*A61M 39/00* (2006.01)
*A61M 39/02* (2006.01)
*A61M 39/10* (2006.01)
*A61M 39/24* (2006.01)
*A61M 39/26* (2006.01)

(52) U.S. Cl.
CPC .............. *A61M 2039/027* (2013.01); *A61M 2039/0285* (2013.01); *A61M 2039/2433* (2013.01); *A61M 2205/0205* (2013.01)

(56) References Cited

U.S. PATENT DOCUMENTS

| | | | |
|---|---|---|---|
| 6,221,065 B1* | 4/2001 | Davis | A61M 5/36 604/905 |
| 8,426,348 B2 | 4/2013 | Ou-Yang | |
| 8,512,294 B2 | 8/2013 | Ou-Yang et al. | |
| 8,574,660 B2 | 11/2013 | Weaver et al. | |
| 8,821,862 B2 | 9/2014 | Madhyastha et al. | |
| 9,149,624 B2 | 10/2015 | Lewis | |
| 9,216,440 B2 | 12/2015 | Ma et al. | |
| 9,399,125 B2 | 7/2016 | Burkholz | |
| 9,695,323 B2 | 7/2017 | Lin et al. | |
| 9,981,069 B2 | 5/2018 | Modak et al. | |
| 10,149,971 B2 | 12/2018 | Liu et al. | |
| 10,220,419 B2 | 3/2019 | Ryan et al. | |
| 10,376,686 B2 | 8/2019 | Burkholz et al. | |
| 10,391,295 B2 | 8/2019 | Ryan et al. | |
| 2003/0209681 A1* | 11/2003 | Leinsing | A61M 39/26 604/905 |
| 2005/0010177 A1* | 1/2005 | Tsai | A61M 39/26 604/256 |
| 2006/0027270 A1* | 2/2006 | Truitt | F16K 15/141 604/537 |
| 2006/0287722 A1* | 12/2006 | Nelson | A61F 2/203 623/9 |
| 2007/0293822 A1* | 12/2007 | Crawford | G09F 3/0291 604/175 |
| 2008/0027410 A1 | 1/2008 | Harding et al. | |
| 2009/0324738 A1 | 12/2009 | Krongauz | |
| 2010/0135949 A1 | 6/2010 | Ou-Yang | |
| 2014/0276456 A1* | 9/2014 | Eddy | A61L 29/06 604/249 |
| 2015/0231309 A1 | 8/2015 | Bihlmaier et al. | |
| 2015/0306368 A1 | 10/2015 | Lin et al. | |
| 2016/0287758 A1 | 10/2016 | Thiagarajan et al. | |
| 2017/0042636 A1 | 2/2017 | Young | |
| 2017/0120028 A1 | 5/2017 | Burkholz et al. | |
| 2017/0281824 A1 | 10/2017 | Ryan | |
| 2018/0250504 A1 | 9/2018 | Schultz | |
| 2019/0134151 A1 | 5/2019 | Bond et al. | |
| 2019/0160275 A1 | 5/2019 | Funk et al. | |
| 2019/0175794 A1 | 6/2019 | Meng et al. | |
| 2019/0217077 A1 | 7/2019 | Chambers | |
| 2019/0232039 A1 | 8/2019 | Erekovcanski et al. | |
| 2019/0234540 A1 | 8/2019 | Marici et al. | |
| 2019/0282795 A1 | 9/2019 | Fangrow | |
| 2019/0308006 A1 | 10/2019 | Erekovcanski et al. | |
| 2019/0344064 A1 | 11/2019 | Buchanan | |
| 2020/0139104 A1* | 5/2020 | Ziebol | A61K 9/0019 |
| 2020/0214900 A1* | 7/2020 | Waller | A61M 25/02 |

FOREIGN PATENT DOCUMENTS

| | | |
|---|---|---|
| WO | WO-2015164134 A2 | 10/2015 |
| WO | 2019178560 | 9/2019 |
| WO | 2018204206 | 11/2019 |

OTHER PUBLICATIONS

Written Opinion of the International Preliminary Examining Authority for Application No. PCT/US2021/016668, dated Jan. 24, 2022, 7 pages.

International Preliminary Report on Patentability from the International Preliminary Examining Authority for Application No. PCT/US2021/016668, dated Apr. 25, 2022, 15 pages.

* cited by examiner

«NEEDLELESS ACCESS CONNECTOR WITH ANTIMICROBIAL RESISTANT VALVE»

TECHNICAL FIELD

The present disclosure generally relates to needleless connectors, and, in particular, to needleless connectors an antimicrobial resistant valve.

BACKGROUND

Needleless access connectors (NAC) are widely used throughout the medical industry to connect and disconnect sources of medical fluid (e.g., a saline solution or a liquid medication) intended to be infused to a patient. Such connectors are commonly used with intravenous (IV) catheters connected through an arrangement of flexible tubing and fittings, commonly referred to as an "IV set", to a source of fluid, for example, an IV bag.

Bacteria and other microorganisms may gain entry into a patient's vascular system from access hubs and ports/valves upon connection to the NAC. Each access hub (or port/valve or connection) is associated with some risk of transmitting a catheter related bloodstream infection (CRBSI), which can be costly and potentially lethal.

To decrease catheter-related bloodstream infection (CRBSI) cases and to ensure connectors are used and maintained correctly, standards of practice have been developed, which include disinfecting and cleaning procedures. For example, the 2016 Infusion Nurses Standards (INS) guidelines recommend that needleless connectors should be consistently and thoroughly disinfected using alcohol, tincture of iodine or chlorhexidine gluconate/alcohol combination prior to each access.

The disinfection of the needleless connector is ultimately intended to aid in the reduction of bacteria that could be living on the surface and possibly lead to a variety of catheter related complications including the CRBSI events described before. Nurses will typically utilize a 70% IPA alcohol pad to complete this disinfection task by doing what is known as "scrubbing the hub." However, compliance to this practice and its efficacy do not appear rigorous. In addition, health care professionals tend to change NAC connectors often, e.g., at least weekly, to reduce infection due to potential build-up of bacteria. However, a continuing need exists to reduce potential bacterial infection and to extend the service life of needleless access connectors.

SUMMARY

Aspects of the subject technology relate to needleless access connectors having a valve that can resist bacterial growth and in particular to needleless access connectors having access ports with an antimicrobial resistant valve.

In some aspects, a NAC valve comprises a head portion and a body portion extending distally from the head portion, the head portion having a top surface, wherein an antimicrobial agent is disposed on various surfaces of the valve or in the valve. In other aspects, an insert is included in the valve which comprises an antimicrobial agent. In further aspects, the valve is the only component of the needleless access connector including an antimicrobial agent.

Embodiments include one or more of the following features individually or combined. For example, the valve can comprise, including its top surface, a silicone elastomer. In some embodiments, the valve can have a porous top surface and includes an insert near the porous top surface of the valve, wherein the insert comprises an antimicrobial coating thereon which includes the antimicrobial agent. Further, the insert can have a top surface that is flat and near the porous top surface of the valve. In other embodiments, the valve can have a series of tunnels or bores within the top surface of the valve and the tunnels and/or bores contain an antimicrobial formulation including the antimicrobial agent. Alternatively, or in addition, the valve can have a series of groves or textured pattern containing an antimicrobial formulation including the antimicrobial agent. Further, the valve can comprise a material that includes the antimicrobial agent, e.g., the valve can comprise a silicone elastomer, a fluoropolymer and the antimicrobial agent. In still further embodiments, the valve material can include the antimicrobial agent by injecting an antimicrobial formulation into a top surface of the valve. In still other embodiments, the antimicrobial formulation can be a sustained release antimicrobial formulation and can include a biodegradeable polymer, a mesh forming polymer, a temperature/pH sensitive polymer or combinations thereof or polymer forming components such as curable adhesive components. The antimicrobial agent can be included in a coating on or in the valve and the antimicrobial agent can comprise about 0.5 to about 50 parts by weight compared to 100 parts by weight of a formulation used to form the coating.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1A is a three-dimensional view showing components of the needless access connector in unassembled form. FIGS. 1B and 1C are cut-away views of the assembled needless access connector showing closed and open states, respectively.

FIG. 2A shows a valve to a NAC having an insert near a porous top surface of the valve. FIG. 2B shows an insert that has a top surface that includes pockets or crevices.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to needleless access connectors (NAC) having a valve, e.g., a valve made of a silicone elastomer, comprising an antimicrobial agent. In some aspects of the present disclosure, the valve has an insert that comprises an antimicrobial coating thereon which includes the antimicrobial agent, and/or physical features, such as a series of tunnels or groves or a patterned surface, containing an antimicrobial formulation including the antimicrobial agent and/or the valve is made of a material that includes the antimicrobial agent.

Advantageously, though not exclusively, the valve is the only component of the needleless access connector including an antimicrobial agent. Needleless access connectors having a valve, which is the only component of the needleless access connector including an antimicrobial agent can reduce the amount of antibiotic available with flow of medical fluid through the connector and thus reduces the antibiotic load on a patient using such an NAC. Reducing antibiotic load is particularly advantageous when more than one NAC is used to deliver fluids to a patient. In addition, valves including a sustained release antimicrobial coating advantageously can extend the service life of the NAC thereby reducing the need for frequent replacements of the NAC over a given period of time.

Figure 1A:
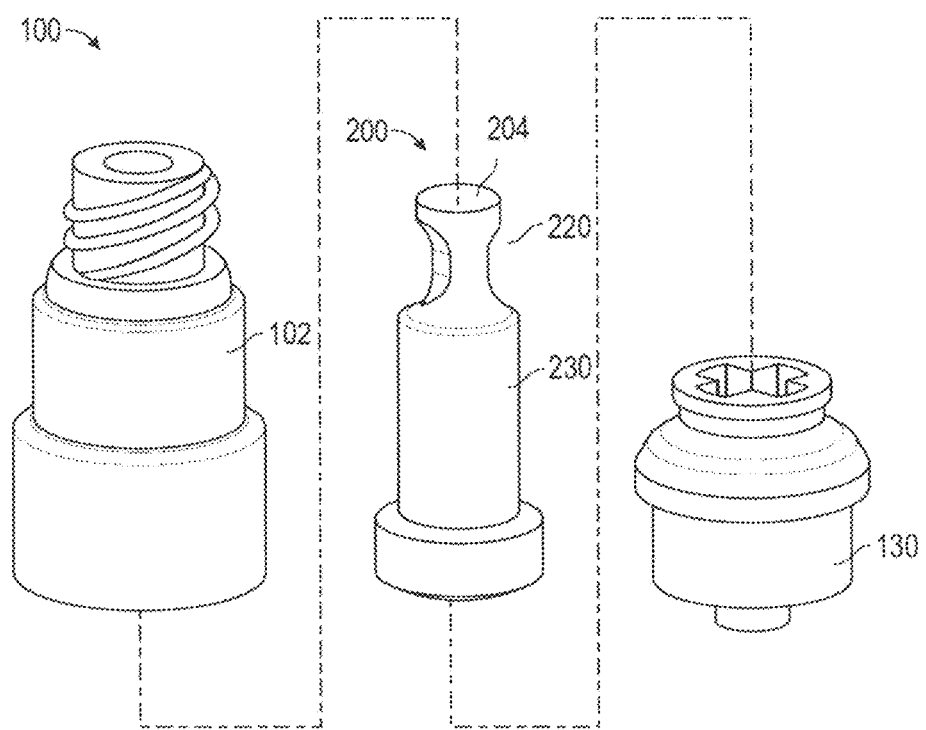
FIGS. 1A-1C are views of an example needless access connector.
Figure 1B:
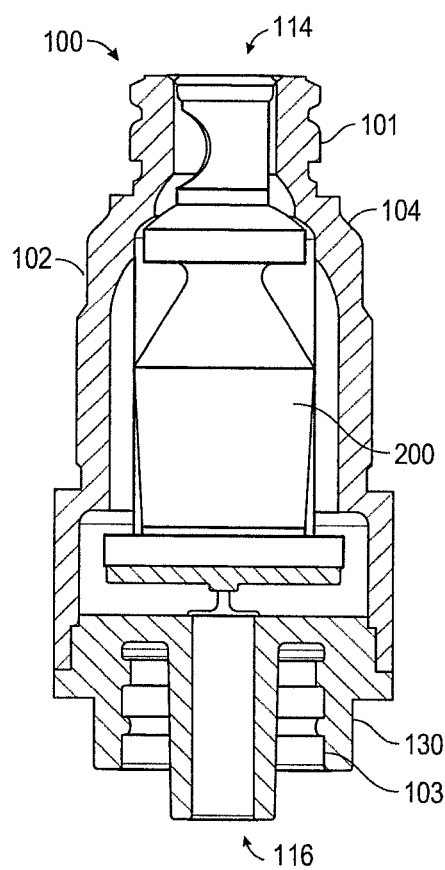
Figure 1C:
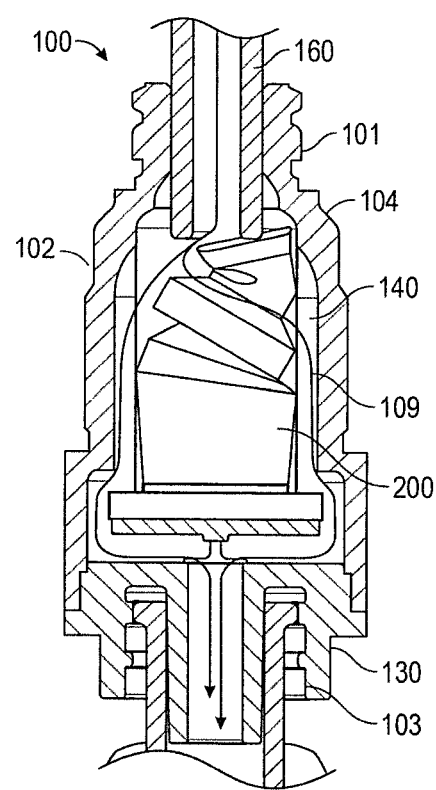

An example needleless access connector employing a valve is shown in FIGS. 1A-1C. FIG. 1A is a three-dimensional view showing components of a needless access connector 100 in unassembled form. FIGS. 1B and 1C are cut-away views of the assembled needleless access connector 100 showing closed and open states, respectively. As depicted for this example, needleless access connector 100 includes housing 102, which has proximal end 104 defining access port 114 and a distal end 106 defining outlet port 116 of housing 102. As referred to herein, proximally refers to an orientation toward top access port 114 of the housing 102, and distally refers to an orientation toward the base portion 106 or bottom of the housing 102, opposite the top access port 114.

Housing 102 includes an internal cavity 140 which extends at least partially between the proximal and distal ends 104 and 106, respectively. Needleless access connector 100 also includes compressible valve 200 disposed within internal cavity 140 of housing 102. Compressible valve 200 includes head portion 220 and compressible body portion 230 extending distally from the head portion 220. For this example, compressible valve is shown with a notched configuration in the head portion but notches are needed to practice the various aspects of the present disclosure.

Access port 114 can include engagement features 101 for coupling to another device (e.g., a fluid transfer assembly). For example, engagement features 101 may include cooperating mechanical elements, such as internal or external surface threads, detents, bayonet-type locking elements, etc., as well as other surface configurations, such as a tapered Luer surface for frictional engagement. In some embodiments, the inlet port 114 may define a female luer fitting with luer lock threading 101. In some embodiments, the outlet port 116 may include engagement features for coupling to another device or coupling to interconnect tubing. For example, the outlet port 116 may comprise a male luer-taper fitting and luer lock threading 103 for medical device implement interconnection. However, engagement features of the outlet port 116 may include other cooperating mechanical elements. In operation, a fluid pathway may be established through needleless connector from the access port 112 to the outlet port 108 for example.

In operation, compressible valve 200 of the needleless connector can compress and collapse when an axial force is applied to the top surface 204 of the compressible valve 200 and the valve can expand and realign when the axial force is removed. Hence, when an axial force (F) is applied to top surface 204 of the valve, the valve (200) compress within internal cavity 130 of housing 102 allowing a fluid path from access port 114 to outlet port 116. As the example depicted in FIG. 1C, a male luer fitting 160, which has a hollow member (as shown in FIG. 1C), can be connected to access port 114 through female fittings 101. The insertion of male luer 160 collapses valve 200 down into internal cavity 130 to break a seal between head portion 220 of valve 200 and open a fluid flow path 109 from access port 114 to outlet port 116. FIG. 1C shows collapsible valve 200 in the collapsed position after insertion of male luer 160 into female luer 101. Male luer 160 delivers fluid, e.g., from an IV bag, which flows through the internal cavity 130, around valve element 200, into channels in male luer fitting 103, and into the catheter or female luer.

Housing 102, can comprise one or more rigid polymeric materials such as a polycarbonate (PC), a polyurethane (PU), a polyvinyl chloride (PVC), a styrene-butadiene rubber (SBR), a polyacrylic or acrylate, or combinations thereof. Valve 200, including head portion 220 and top surface 204, can comprise an elastic, inert material, such as a silicone elastomer, so that it is collapsible within the housing 102 and resists adversely interacting with medicinal fluids.

While current designs for NAC are robust to resist bacterial ingress, the access port is of particular concern since it is typically exposed to the environment when not connected to a medical implement. However, NAC with a valve comprising an antimicrobial agent, particularly on a top surface of the valve, also referred to as a face side and access port side of the valve, bacterial formation or build-up can be minimized or eliminated and these conditions can be maintained for an extended period of time, e.g., for one or more weeks of use. Hence in an aspect of the present disclosure, an NAC has a valve, e.g. a valve comprising a silicone elastomer, including an antimicrobial agent, such as by a sustained release antimicrobial coating or formulation on or within the valve.

Figure 2A:
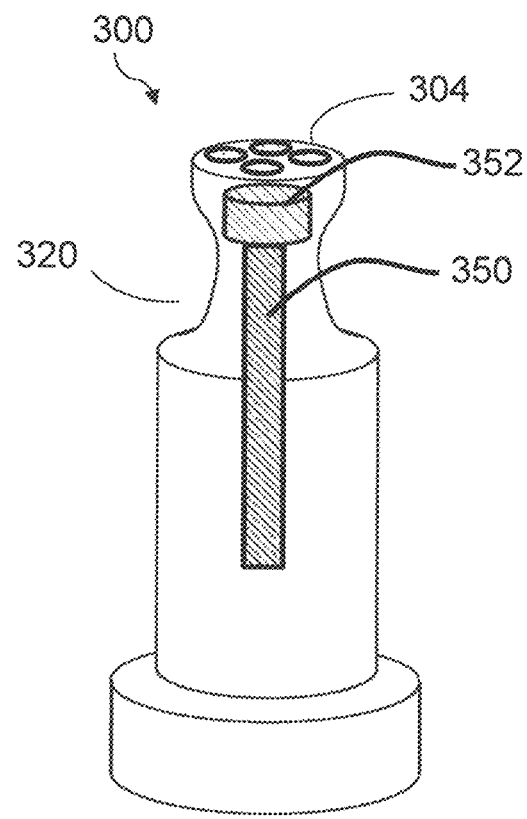
FIGS. 2A and 2B are views of an example valve to a needless access connector.
Figure 2B:
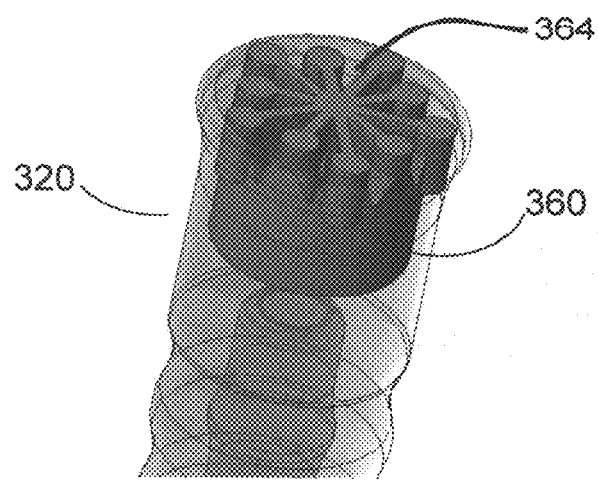

In an aspect of the present disclosure, an insert having an antimicrobial coating is included within a valve of an NAC. The insert can be included near a top surface of the valve. An example needleless access connector employing a valve having an insert is shown in FIGS. 2A and 2B. In such an embodiment, valve 300 includes pore on its top surface 304 (e.g., a porous top surface) of head portion 320 of valve 300 so that an antimicrobial agent can leach from the insert through the valve to an exterior surface of the valve In addition, the porous top surface can also allow liquids to access the insert, such as an aqueous medical fluid, disinfecting fluid or other fluids, allowing an aqueous antimicrobial agent, e.g. a chlorhexidine salt, to leach out from the insert and eradicate microbes.

In some embodiments, the insert can have a flat top (depicted as 352 in FIG. 2A) and placed such that the flat top is substantially parallel with a top, porous surface of a head portion of a NAC valve (e.g., 304). Further, or alternatively, the insert can include pockets or crevices which can act as a reservoir for an antimicrobial coating placed thereon. FIG. 2B shows an example insert 360 with top surface that includes pockets or crevices (364) for containing an antimicrobial coating or formulation in the pockets or crevices. For this example, insert 360 is included in head portion 320 of the valve and the top of the valve would include a porous top surface (not shown). The pockets or crevices of the insert can advantageously facilitate keeping the insert in place within the valve due to gripping of an over-molded valve material in and/or around the pockets or crevices.

In certain embodiments of the present disclosure, the insert can be rigid and can comprise one or more rigid polymeric materials such as a polycarbonate (PC), a polyurethane (PU), a polyvinyl chloride (PVC), a styrene-butadiene rubber (SBR), a polyacrylic or acrylate, or combinations thereof. A rigid insert has an advantage that can such an insert in a top portion of the valve can make the top surface of the valve more rigid and less prone to conforming around an implement, e.g., syringe, that is connected to the access port thereby facilitating a consistent or wider flow path for fluid transmitted through the NAC.

Figure 3:
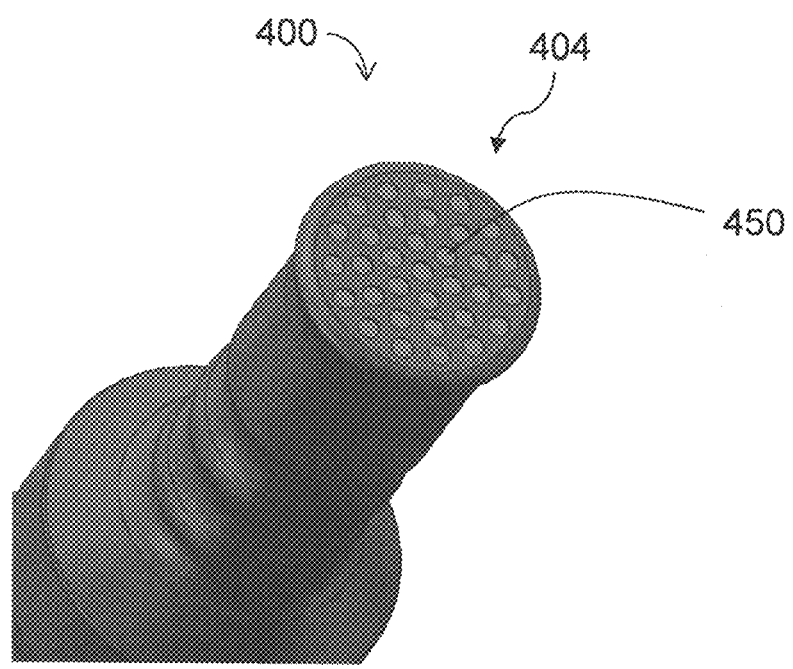
FIG. 3 shows an example valve to a needless access connector with physical features on its top surface that can contain an antimicrobial coating or formulation.

In another aspect of the present disclosure, a valve of an NAC can have physical features, such as a series of tunnels or groves or a patterned surface, containing an antimicrobial formulation including the antimicrobial agent. For example and as depicted in FIG. 3, valve 400 of an NAC can have a series of tunnels or bores (450) within top surface (404) of the valve, which can be made by molding a valve with such features. These tunnels and/or bores can contain, by filling or otherwise, an antimicrobial formulation including an antimicrobial agent, e.g., a chlorohexidine salt formulated with an adhesive.

In another aspect of the present disclosure, a valve of an NAC can have a series of groves on a surface thereof. The groves can be on a top surface on a head portion of the valve and/or on a body surface of the valve. Such groves can be formed as a micro-pattern and/or textured surface of the valve. Such groves/micro-patterns can be molded into the part. The groves can then be filled with an antimicrobial formulation including an antimicrobial agent, e.g., a chlorohexidine salt formulated with an adhesive, resulting in a valve with a series of groves or textured pattern containing the antimicrobial formulation including the antimicrobial agent. Upon contact of a valve having an antimicrobial coating within or on physical features by an aqueous fluid, a water soluble antimicrobial agent contained in the coating can be released from the valve providing antibacterial properties to the contacting fluid and surrounding surfaces.

In another aspect of the present disclosure, a valve of an NAC can have one or more hydrophilic surfaces and an antimicrobial coating including an antimicrobial agent on the one or more hydrophilic surfaces.

As described above, a valve of an NAC can include a head portion and body portion. Such valves are typically made from inert materials such as a silicone elastomer. However, adhering a sustained release antimicrobial coating on such materials is challenging due to the relative inertness and flexibility needed for valves. To better include an antimicrobial agent with such valves, the surface thereof can be modified.

Hence in an aspect of the present disclosure, the surface of the valve is treated to make the surface more hydrophilic than an untreated surface. Such treatments can include, for example, treating with an alcohol such as isopropyl alcohol (IPA). The surface can also be made more hydrophilic by treating the surface of the valve with a plasma of oxygen, argon or both. The surface can be made more hydrophilic by applying a primer to the surface of the valve followed by applying an antimicrobial coating, e.g., an adhesive antimicrobial formulation (UV curable silicone adhesive: urethane acrylate curable adhesive formulation with CHA/CHG.). Such primers can be obtained from companies such as Henkel and Loctite, for example.

Another way to facilitate including an antimicrobial agent with a valve of an NAC is to roughen the valve surface for better adhesion of an antimicrobial coating. Further, the surface can be subjected to an ionized bombardment of the antimicrobial agent, e.g., CHA to modify the surface.

In another aspect of the present disclosure, a valve of an NAC can include an antimicrobial agent as part of the valve material. Preferably the antimicrobial agent is more or less uniformly dispersed within the valve material. One way to achieve this is to compound a valve material, e.g., a silicone elastomer, with an antimicrobial agent. Other polymeric components can also be compounded with the valve material and antimicrobial agent. Such polymeric components include, for example, inert materials such as a fluoropolymer, e.g., polytetrafluoroethylene (PTFE), a hydrophilic polymer such as polyvinylpyrolidone (PVP). Hydrophilic polymers can have the advantage in that they can bloom to the surface, e.g., when such a material is contacted with an aqueous fluid, the hydrophilic polymer has a propensity to bloom to the surface which can then elute the antimicrobial agent.

Another way to include an antimicrobial agent as part of the valve material is to mix a silicone elastomer with another silicone material that has hydrophilic chains to form a valve having hydrophilic surfaces Another way to include an antimicrobial agent as part of the valve material is to imbibe a valve with a solution including an antimicrobial agent to thereby swell the valve and cause the agent to seek into the material. For example a valve composed of a silicone elastomer can be submerged in a solution of antimicrobial agent such as a chlorhexidine salt. The valve swells in the solution allowing some of the antimicrobial agent to seep into the valve material.

Another way to include an antimicrobial agent in a NAC valve is to inject an antimicrobial formulation into the top surface of the valve or port face such as by use of hypodermic needles. Once the needles are inserted into the top surface of the valve, a mixture of chlorhexidine/adhesive is injected. The mixture continues to be injected even as the needles are being extracted filling the voids left by the needles.

Useful antimicrobial agents that can be included in valves of NAC or with formulations for preparing antimicrobial coatings of the present disclosure include, for example, aldehydes, anilides, biguanides, silver element or its compounds, bis-phenols, and quaternary ammonium compounds and the like or combinations thereof. In particular, suitable antimicrobial agents of the present disclosure include, for example, a triclosan, a chlorhexidine salt such as chlorhexidine gluconate (CHG), chlorhexidine acetate (CHA), a chlorhexidine phosphanilate, a silver salt, a chlorhexidine/silver sulfadiazine.

Useful antimicrobial coatings or fain ulations of the present disclosure include one or more antimicrobial agents with one or more polymers. Alternatively, or in combination with one or more antimicrobial agents and polymers, the formulation can include polymer forming components, e.g. UV curable monomers and/or oligomers. In some embodiments, the polymeric component of a formed antimicrobial coating or formulation are such that they can release the antimicrobial agent over time, e.g., a sustained release coating or formulation that can release the antibiotic agent over time such as over a period of at least 7 days, 14 days, 21 days, etc. The molecular weight of the polymer of the formed coating can be adjusted to control the release rate of the antimicrobial agent.

Useful polymers that can be included in formulations for preparing antimicrobial coatings of the present disclosure include, for example, biodegradeable polymers such as poly(lactic-co-glycolic acid) (PLGA), polycaprolactone (PCL), polyglycolide (PGL), polylactic acid (PLA), poly-3-hydroxybutyrate (PBH), polysaccharides, polyethylene glycol (PEG), polyethyleneoxide (PEO), mesh forming polymers such as cellulose acetate, temperature/pH sensitive polymers such as hyaluronic acid, poly(N-isopropylacrylamide) (NIPPam) etc. or co-polymers thereof and/or combinations thereof.

Useful polymer forming components that can be included in formulations for preparing sustained release antimicrobial coatings of the present disclosure include, for example, moisture or temperature curable adhesive components such as a cyanoacrylate, UV curable adhesives such as urethane acrylate curable adhesives. The curable adhesive components can be formulated with one or more antimicrobial agents. UV curable formulation can include a combination of a urethane or a polyester-type oligomer with acrylate-type functional groups, acrylate-type monomers, and antimicrobial agents with optional photoinitiators, rheological modifiers, and additives. The antimicrobial agents are preferably uniformly and distributed throughout the whole coating matrix A wide variety of UV curable oligomers can be used with formulations of the present disclosure. For example, the oligomers can be acrylated aliphatic urethanes, acrylated aromatic urethanes, acrylated polyesters, unsaturated polyesters, acrylated polyethers, acrylated acrylics, and the like, or combinations of the above. The acrylated functional group can be mono-functional, di-functional, tri-functional, tetra-functional, penta-functional, or hexa-functional.

As with the oligomers, a wide range of monomers can be used with formulations of the present disclosure Such monomers include, for example, 2-ethyl hexyl acrylate, isooctyl acrylate, isobornylacrylate, 1,6-hexanediol diacrylate, diethylene glycol diacrylate, triethylene glycol diacrylate, pentaerythritol tetra acrylate, penta erythritol tri acrylate, dimethoxy phenyl acetophenone hexyl methyl acrylate, 1,6 hexanidiol methacrylate, and the like, or combinations thereof.

To facilitate UV-curing, UV curable formulations can include an adequate and compatible photoinitiator. Such photoinitiators can be: 1) single molecule cleavage type, such as benzoin ethers, acetophenones, benzoyl oximes, and acyl phosphine oxide, and 2) hydrogen abstraction type, such as Michler's ketone, thioxanthone, anthroguionone, benzophenone, methyl diethanol amine, 2-N-butoxyethyl-4-(dimethylamino) benzoate, and the like, or combinations thereof. The UV curable formulation can be rapidly cured with ultraviolet light, e.g., curing can be completed in seconds or minutes depending on the formulation and curing conditions. The sustained release coatings of the present disclosure are generally efficacious within minutes.

The antimicrobial agent can be included in a formulation the present disclosure in the amount of from about 0.5 to about 50 parts by weight in compared to 100 parts by weight of the formulation used to form the coating, e.g., in the amount of from about 0.5 to about 30 parts by weight of the formulation, such as from about 1 to about 20 parts by weight.

Some particular formulations that can be applied include, for example, a urethane acrylate adhesive or a cyanoacrylate adhesive with about 8 wt % CHA which can be applied to a surface of a NAC valve. In addition, a surface of a valve for an NAC can be subjected to a primer, such as a primer for a silicone valve available from companies such as Henkel and Loctite, followed by applying the formulation including 8% CHA and curing the formulation to form a sustained release antimicrobial coating on the valve. A silicone valve can be made more hydrophilic/wettable by plasma treatment or the valve can be etched so that an acrylate urethane adhesive formulation can be coated onto a silicone valve.

Formulations for preparing sustained release coatings of the present disclosure can be prepared by mixing an antibacterial agent with a polymer, with or without solvent, to form a slurry or solution. Alternatively to mixing the antibacterial agent with a polymer, or in combination thereof, the antibacterial agent can be mixed with polymer forming components to prepare a formulation for preparing sustained release coatings. The formulation can then be applied to top surfaces by spray coating, dip coating, and/or wiping the formulation onto the surface. For example, a curable formulation for preparing a sustained release antimicrobial coating according to certain aspects of the present disclosure can be prepared by combining polymer forming components, e.g., a cyanoacrylate, with about 8 wt % of an antimicrobial agent, e.g., fine powder of CHA (CHA can be ground to a small mesh/pore size so that it can mix to form an uniform distribution of the CHA in the formulation), to make a slurry. The slurry can then be applied to a valve of a NAC.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless access connector having a compressible valve comprising an antimicrobial agent,
    wherein the compressible valve is configured to allow a fluid path around the compressible valve through the needleless access connector when the compressible valve is collapsed and compressed under application of axial force, and close the fluid path through the needleless access connector when the axial force is removed,
    wherein the valve has a porous top surface and includes an insert near the porous top surface of the valve, wherein the insert comprises an antimicrobial coating thereon which includes the antimicrobial agent.

2. The needleless access connector of claim 1, wherein a top surface of the valve comprises a silicone elastomer.

3. The needleless access connector of claim 1, wherein the insert has a top surface that is flat and near the porous top surface of the valve.

4. The needleless access connector of claim 1, wherein the insert has a top surface that includes pockets or crevices and the antimicrobial coating is included in the pockets or crevices.

5. The needleless access connector of claim 1, wherein the insert is rigid and comprises a rigid polymeric material.

6. The needleless access connector of claim 1, wherein the valve has a series of tunnels or bores within the top surface of the valve and the tunnels and/or bores contain an antimicrobial formulation including the antimicrobial agent.

7. The needleless access connector of claim 1, wherein the valve has a series of groves or textured pattern containing an antimicrobial formulation including the antimicrobial agent.

8. The needleless access connector of claim 1, wherein the valve has an antimicrobial coating including the antimicrobial agent on a hydrophilic surface of the valve.

9. The needleless access connector of claim 1, wherein the valve is made of a material that includes the antimicrobial agent.

10. The needleless access connector of claim 9, wherein the valve material comprises a silicone elastomer, a fluoropolymer and the antimicrobial agent.

11. The needleless access connector of claim 9, wherein the valve material includes the antimicrobial agent by injecting an antimicrobial formulation into a top surface of the valve.

12. The needleless access connector of claim 11, wherein the antimicrobial formulation is a sustained release antimicrobial formulation.

13. The needleless access connector of claim 12, wherein the sustained release antimicrobial formulation comprises a biodegradeable polymer, a mesh forming polymer, a temperature/pH sensitive polymer or combinations thereof.

14. The needleless access connector of claim 1, wherein the antimicrobial agent is included in a coating formed from a cyanoacrylate.

15. The needleless access connector of claim 1, wherein the antimicrobial agent comprises a chlorhexidine salt.

16. The needleless access connector of claim 1, wherein the antimicrobial agent is included in a coating on the valve and the antimicrobial agent comprises about 0.5 to about 50 parts by weight compared to 100 parts by weight of a formulation used to form the coating.

17. A needleless access connector having a compressible valve comprising an antimicrobial agent, wherein the compressible valve is the only component of the needleless access connector including an antimicrobial agent,
wherein the compressible valve is configured to allow a fluid path around the compressible valve through the needleless access connector when the compressible valve is collapsed and compressed under application of axial force and close the fluid path through the needleless access connector when the axial force is removed,
wherein the valve has a porous top surface and includes an insert near the porous top surface of the valve, wherein the insert comprises an antimicrobial coating thereon which includes the antimicrobial agent.

18. The needleless access connector of claim 17, wherein only a top surface of the valve includes the antimicrobial agent.

19. The needleless access connector of claim 17, wherein the antimicrobial agent is included in a coating formed from a cyanoacrylate.

* * * * *